United States Patent
DeMassa et al.

(10) Patent No.: US 6,287,483 B1
(45) Date of Patent: *Sep. 11, 2001

(54) METHOD OF STABILIZING UNSATURATED ORGANIC COMPOUNDS FROM POLYMERIZATION

(75) Inventors: John M. DeMassa, South Norwalk, CT (US); Stephen M. Fagan, Newtonville, MA (US)

(73) Assignee: Uniroyal Chemical Company, Inc., Midddlebury, CT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/084,619

(22) Filed: May 26, 1998

(51) Int. Cl.$^7$ .................... C09K 15/22; C07D 233/00
(52) U.S. Cl. ............................ 252/401; 252/403
(58) Field of Search ...................... 252/403, 401

(56) References Cited

U.S. PATENT DOCUMENTS

| | | | | |
|---|---|---|---|---|
| 1,805,953 | * | 5/1931 | Morton ............................... | 252/403 |
| 2,851,415 | | 9/1958 | Hughes . | |
| 2,968,630 | * | 1/1961 | Pillon et al. ......................... | 252/403 |
| 3,089,761 | * | 5/1963 | Andress ............................... | 252/403 |
| 3,732,244 | | 5/1973 | Boocock et al. . | |
| 3,733,326 | | 5/1973 | Murayama et al. . | |
| 3,799,942 | | 3/1974 | Boocock et al. . | |
| 4,043,973 | * | 8/1977 | Wang et al. ......................... | 252/403 |
| 4,208,525 | | 6/1980 | Rasberger et al. . | |
| 4,665,185 | | 5/1987 | Winter et al. . | |
| 4,670,131 | | 6/1987 | Ferrell . | |
| 4,970,341 | | 11/1990 | Summerford . | |
| 5,214,112 | | 5/1993 | Shimizu et al. . | |
| 5,258,138 | | 11/1993 | Gatechair et al. . | |
| 5,374,729 | | 12/1994 | Galbo . | |

FOREIGN PATENT DOCUMENTS 1337291  11/1973  (GB) .
WO9845385  10/1998  (WO) .

OTHER PUBLICATIONS

Chemical Abstract. vol. 105. No. 12. (Sep. 22, 1986) entitled "Inhibiting Effect of a Nitroxyl Radical in Polymerization of Styrene and Methyl Methacrylate in Neutral and Acid Media" by Goldfein et al. appearing at p. 3, col. 1. XP–002111973.

Database WPI–Section Ch, Week 7833. Derwent Publications Ltd. Class A60, AN 78–60166a. XP002111904 & SU 574 443 A (Novosibirsk Prg.Chem.Inst.) Nov. 9, 1977.

Database WO I. Section Ch, Week 7131. Derwent Publications Ltd., Class A61, AN 71–51161s XP002111905 & SU 282 330 A (Novosibirsk Org.Chem.Inst.).

WO 98 45385 A (Rhodia–Chimie) Oct. 15, 1998. Claims; examples 2,3.

Volodarsky et al., "Synthesis and Reactions of α–Hydroxy-lamino–oximes–oximes" Institute of Organic Chemistry, Siberian Division of the Academy of Sciences of the U.S.S.R., Novosibirsk, U.S.S.R. (1986) Month Unknown.

Goldfein et al., "Inhibiting Effect of a Nitroxyl Radical in Polymerization of Styrene and Methylmethacrylate (MMA) in Neutral and Acid Media" T2V. Vyssh. Uchebn. Zaved., Khim. Tekhnol., 29(4), 93–7 (Chemistry of Synthetic High Polymers) (1986) Month Unknown, Considered English Abstract Only.

* cited by examiner

Primary Examiner—Margaret Medley
(74) Attorney, Agent, or Firm—Raymond D. Thompson; Peter G. Dilworth

(57) ABSTRACT

A method for stabilizing an unsaturated polymerizable organic compound from premature polymerization includes addition thereto of an imidazoline or imidazolidine compound, optionally with ring substituents including hydroxyl, oxyl, or oxide moieties as well as aliphatic, alicyclic and/or heterocyclic moieties.

24 Claims, No Drawings

METHOD OF STABILIZING UNSATURATED ORGANIC COMPOUNDS FROM POLYMERIZATION

BACKGROUND OF THE INVENTION

1. Technical Field

The present invention relates to a method for stabilizing unsaturated organic compounds from polymerization and to a monomeric composition containing a polymerization inhibitor.

2. Background of the Art

The ethylenically unsaturated compounds which can be polymerized by free radical initiation are commonly called monomers. They constitute a major class of industrial chemicals. Because of the presence of the polymerizable double bond, the widespread sources of initiating radicals from peroxides, light and/or thermal generation, such monomers are prone to undesirable and premature polymerization at various stages during their manufacture, purification, storage, shipping, blending and use. Protection of such monomers from such premature polymerization is needed up to the point where polymerization is actually desired. If premature polymerization does occur, the monomer may suffer contamination by polymer, troublesome increase in viscosity, gelation and/or loss of reactivity. Fouling of distillation equipment including heat exchanger surfaces, storage vessels, transfer lines, pumps, shipping containers and application equipment can occur with ensuing costs of cleaning, downtime, loss of material and unnecessary labor costs. Premature polymerization can also constitute a safety hazard since uncontrolled exothermic polymerization can cause ruptured vessels, atmospheric contamination, and in extreme cases, explosions and fires. Deterioration of monomers in shipping and storage may also make necessary the use of costly refrigerated shipping and storage facilities.

A further problem is that of undesired free radical polymerization of unsaturated monomers which occur in commercial products such as hydrocarbon fuels and refinery streams. In these cases, polymerization accompanied by the incorporation of oxygen moieties leads to gum and sludge deposits which can foul carburetors, engines, fuel tanks or fuel lines. In refineries, such monomers in hydrocarbon streams such as cracking products can foul pipelines, valves, pumps, heat exchanges, stills and storage vessels.

Another problem in regard to undesired polymerization of free radical polymerizable monomers is the case of polymerizations which are intentional, but which must be prevented from going too far. For example, the quality of poly(vinyl chloride) suspension polymer and of synthetic rubber made from olefins and dienes is superior (i.e. better molecular weight distribution, stability, and processing properties) if the polymerization is stopped short of complete consumption of the monomers. It is also desirable to have available in a plant conducting vinyl polymerization reactions some rapid and efficient means for stopping a runaway polymerization if other means such as cooling should fail.

It is known that the addition of certain compounds to monomers can retard or even prevent their undesired polymerization, and that when polymerization of the monomer is desired, the inhibitor can be removed or overridden by a deliberately-added polymerization initiator. Various aromatic compounds have been used as such inhibitors in the prior art. Typical ones are 2,6-dinitro-p-cresol (DNPC), hydroquinone, monomethyl ether of hydroquinone (MEHQ), tert-butylphenols, phenothiazine, phenylenediamines and benzoquinones. These are usually used at a level of 50 to 1000 ppm. These inhibitors are not totally effective, and even with such inhibitors present it is often advisable to store such inhibited monomers in a cool place and for limited periods of time. Moreover, these aromatic inhibitors are a cause of serious discoloration problems in the monomers and in polymers deliberately prepared from such monomers. Typically these aromatic inhibitors produce quinoidal chromophoric groups with very visible light absorbance.

Various other polymerization inhibitors are known. For example, U.S. Pat. No. 5,258,138 to Gatechair et al. discloses the stabilization of ethylenically unsaturated monomers from premature polymerization by adding to the monomer a stabilizing amount of a substituted hindered amine in combination with phenothiazine or other related heterocyclic moiety.

U.S. Pat. No. 4,670,131 to Ferrell discloses that fouling of equipment used for processing organic feed streams containing olefinic compounds can be controlled by inhibiting polymerization of the olefinic compounds by the addition of a stable free radical such as a nitroxide to the feedstream.

SUMMARY

In accordance with the present invention a method for stabilizing a polymerizable unsaturated organic compound from premature polymerization is provided. The method comprises:

adding to the unsaturated organic compound an effective amount, sufficient to prevent premature polymerization, of at least one polymerization inhibitor having the formula:

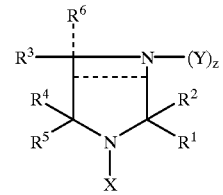

wherein X is —H, —OH, —O•, —NO$_2$, or —CH$_3$,

R$^1$ R$^2$, R$^4$ and R$^5$ are the same or different and each is selected from the group consisting of hydrogen, an aliphatic moiety having from 1 to about 20 carbon atoms, aryl, alkaryl or aralkyl having from 6 to about 12 carbon atoms, alicyclic and heterocyclic, or wherein R$^1$ and R$^2$ together or R$^4$ and R$^5$ together form part of an alicyclic or heterocyclic moiety having from about 4 to about 10 ring members, R$^3$ and optional group R$^6$ are the same or different and each is preferably selected from the group consisting of hydrogen, an aliphatic moiety having from 1 to about 20 carbon atoms, or wherein R$^3$ and R$^6$ together represent oxygen in the form of an oxo (═O) moiety, and wherein the dotted lines each represent an optional supplemental bond, such that where there is no optional supplemental bond within the ring the R$^6$ group is present as a ring substituent, z is 1 and Y is —H, —OH, or —O•, and where there is an optional supplemental bond within the ring, there is no R$^6$ group present as a ring substituent, z is 0 or 1 and where z is 1, Y is O bonded to N in the form of an N→O moiety.

Also provided herein is a composition which includes an ethylenically unsaturated monomer and an effective amount of the polymerization inhibitor described herein.

DETAILED DESCRIPTION

The present method for stabilizing a polymerizable unsaturated organic compound from premature polymerization comprises adding to the unsaturated organic compound an effective amount of a polymerization inhibitor which includes an imidazoline or imidazolidine compound, optionally with hydroxy, oxo, oxyl or oxide substituents, as described more fully below.

The polymerizable organic compound is preferably an ethylenically unsaturated monomer having at least one carbon-carbon double bond capable of undergoing free radical induced polymerization. Particularly advantageous is the stabilization of styrene. The unsaturated organic compound can be neat (i.e., undiluted) or admixed with a solvent such as toluene, benzene, ethylbenzene, styrene or water.

Typical examples of such monomers are olefinic and vinyl aromatic compounds including, but not limited to, styrene, methylstyrene, divinylbenzene, dienes such as butadiene and isoprene; halogenated monomers such as vinyl chloride, chloroprene, vinylidene chloride, vinylidene fluoride and vinyl fluoride; unsaturated acids such as acrylic acid, methacrylic acid and crotonic acid; unsaturated esters such as vinyl acetate, alkyl acrylates and alkyl methacrylates such as methyl methacrylate, ethyl acrylate, methyl acrylate, 2-hydroxyethyl acrylate and methacrylate, ethylene bismethacrylate, trimethylolpropane triacrylate, acrylated epoxy resin and polyethylene glycol diacrylate; unsaturated amides such as acrylamide, N,N-dimethylacrylamide, methylene-bisacrylamide and N-vinylpyrrolidone; unsaturated nitrile monomers such as acrylonitrile; and unsaturated ethers such as methyl vinyl ether; and miscellaneous monomers such as the vinyl pyridines, diethyl vinylphosphonate and sodium styrenesulfonate.

The method of the instant invention involves simply dissolving an effective inhibiting amount of the inhibitor in the monomer prior to exposure of the latter to conditions where the premature, undesired free radical initiated polymerization might occur.

The polymerization inhibitor can be added prior to any processing steps for example to extend storage life. Alternatively the polymerization inhibitor can be added in any part of the processing equipment, for example to deactivate autocatalytic polymerization of any unsaturated monomer present in the feed stream.

By "effective amount" is meant an amount or concentration sufficient to prevent premature polymerization of the monomer. An effective concentration of the polymerization inhibitor described below can range from 1 ppm to about 10,000 ppm by weight of polymerization inhibitor in the monomer, preferably about 10 ppm to about 1,000 ppm, and more preferably about 50 ppm to about 200 ppm. The lower amount would be used where the degree of inhibition is not great, such as when the monomer is to be used promptly and/or will be stored in a refrigerator, or where the monomer is inherently less prone to polymerize readily, such as those compounds with internal double bonds. Higher concentrations of inhibitor are used where the monomer is stored for long periods of time or in warm conditions, where contamination is likely, where the monomer is likely to be exposed to photoinitiation, or where the monomer (e.g., acrylates, acrylic acid) is prone to polymerization. Those skilled in the art are aware of the relative stability and readiness to polymerize of the various monomers.

The stabilized monomer compositions of the present invention may also contain additional inhibitors, such as hydroquinone, the monomethyl ether of hydroquinone, (these often being required by monomer specifications) or catechol, tert-butylated hydroquinones or catechols, other alkylated phenols, nitrosophenols and nitrosophenylhydroxylamines.

The stabilized compositions may also contain metal deactivators and UV absorbers to improve light stability, stabilizers such as amines to retard acid-catalyzed degradation, thermal or photoinitiators, and/or other conventional additives.

When it is desired to subject the inhibited monomer to polymerization, the inhibitor can either be removed or overridden by sufficient polymerization initiator. Removal can be accomplished by distillation, absorption or washing. The polymerization inhibiting action of the instant compounds can be overridden by use of sufficient free radical initiator, actinic light (e.g., UV) irradiation, electron beam exposure or other polymerization initiating means.

The polymerization inhibitor is a heterocyclic moiety having a five member ring with nitrogen atoms in the first and third ring positions, and carbon atoms in the second, fourth and fifth positions.

The polymerization inhibitor has a structure as indicated by formula I:

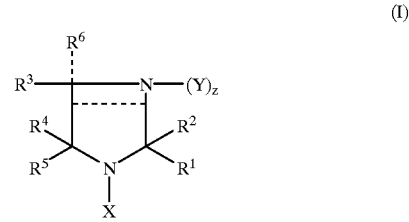

wherein X is a substituent attached to the nitrogen atom in the first ring position and can be hydrogen (—H), hydroxyl (—OH), oxyl (—O•), nitro (—NO$_2$), or methyl (—CH$_3$).

$R^1$, $R^2$, $R^4$ and $R^5$ are the same or different and each is selected from the group consisting of hydrogen, an aliphatic moiety having from 1 to about 20 carbon atoms, aryl, alkaryl or aralkyl having from 6 to about 12 carbon atoms, alicyclic and heterocyclic, or wherein $R^1$ and $R^2$ together or $R^4$ and $R^5$ together form part of an alicyclic or heterocyclic moiety having from about 4 to about 10 ring members.

$R^3$ and optional group $R^6$ (when present) are the same or different and each is preferably selected from the group consisting of hydrogen and an aliphatic moiety having from 1 to about 20 carbon atoms. Alternatively, $R^3$ and optional group $R^6$ together represent oxygen in the form of an oxo (=O) moiety. In yet another alternative, $R^3$ and optional group $R^6$ can be aryl, alkaryl or aralkyl having from 6 to about 12 carbon atoms, alicyclic or heterocyclic, or $R^3$ and optional group $R^6$ together can form part of an alicyclic or heterocyclic moiety having from about 4 to about 10 ring members.

The dotted lines each represent an optional supplemental bond, such that where there is no optional supplemental bond within the ring (i.e., the nitrogen atom in the third ring position and the carbon atom in the fourth ring position are connected by a single bond) the $R^6$ group is present as a ring substituent, z is 1 and Y is —H, —OH, or O•. Where there is an optional supplemental bond within the ring (i.e., the nitrogen atom in the third ring position and the carbon atom in the fourth ring position are connected by a double bond), there is no $R^6$ group present as a ring substituent, z is 0 or 1. That is, where z is 0 the indicated nitrogen has no substituent attached to it. Where z is 1, Y is an oxygen atom (O) bonded to the ring nitrogen atom (N) as an oxide (N→O) moiety.

In one embodiment the polymerization inhibitor has a structure indicated by formula II:

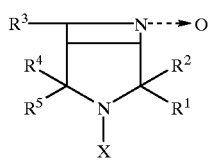

(II)

wherein X is selected from hydroxyl (—OH), hydrogen (—H), oxyl (—O•), nitro (—NO$_2$), and methyl (—CH$_3$).

The nitrogen atom in the third ring position is connected to the carbon atom in the fourth ring position by a double bond. Accordingly, the presence of the oxide substituent (→O) attached to the second nitrogen atom in the third ring position is optional and there is no R$^6$ group.

R$^1$, R$^2$, R$^3$, R$^4$ and R$^5$ are as indicated above. Preferably R$^1$, R$^2$, R$^3$, R$^4$ and R$^5$ each selected from methyl, ethyl, propyl. or butyl groups, and X is selected from hydroxyl or oxyl.

Exemplary compounds of formula II include (but are not limited to): 2,2,4,5,5-pentamethyl-3-imidazoline; 1-oxyl-2,2,4,5,5-pentamethyl-3-imidazoline-3-oxide; 1-oxyl-4-ethyl-2,2,5,5-tetramethyl-3-imidazoline; 1-hydroxy-4-ethyl -2,2,5,5-tetramethyl-3-imidazoline; 1-methyl-2,2,4,4-tetramethyl-3-imidazoline-3-oxide; 1-hydroxy-2-(2,2,6,6-tetramethyl-piperidino-1-oxyl)-4,5,5-trimethyl-3-imidazoline; 1-oxyl-2-cyclohexane-4-ethyl-5,5-dimethyl-3-imidazoline; and 1-hydroxy-2,2,5,5-pentamethyl-3-imidazoline.

In another embodiment the polymerization inhibitor has a structure as indicated by formula Ill:

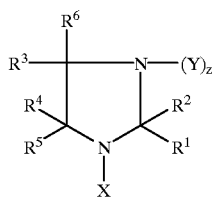

(III)

wherein R$^1$, R$^2$, R$^3$, R$^6$, R$^4$, and R$^5$ are as indicated above. X is as indicated above.

The nitrogen atom in the third ring position is connected to the carbon atom in the fourth ring position by a single bond. Accordingly, Y can be hydrogen (—H), hydroxyl (—OH), or oxyl (—O•).

Preferably, R$^1$, R$^2$, R$^4$ and R$^5$ are each selected from the group consisting of methyl, ethyl, propyl, and butyl, and X is selected from hydroxyl or oxyl. Optionally, R$^3$ and R$^6$ together form an oxo (=O) group.

Exemplary compounds of formula III include, (but are not limited to): 1-oxyl-3-hydroxy-4-oxo-2,2,5,5-tetramethyl-3-imidazolidine, and 1,3-dihydroxy-4-oxo-2,2,5,5-tetramethyl-3-imidazolidine.

In yet another feature of this invention the polymerization inhibitor can include a blend made by mixing a first compound selected from the group consisting of 1-hydroxy-4-ethyl-2,2,5,5-tetramethyl-3-imidazoline, 1-oxyl-2,2,4,5,5-pentamethyl-3-imidazoline-3-oxide, and 1-hydroxy-2,2,4,5,5-pentamethyl-3-imidazoline, and a second compound selected from the group consisting of 1-oxyl-4-ethyl-2,2,5,5-tetramethyl-3-imidazoline and 1-oxyl-2,2,4,5,5-pentamethyl-3-imidazoline.

Imidazolines and imidazolidines can be prepared in accordance with the following outline of procedures:

In a first step a nitrosochloroalkane (Formula IV, below) can be prepared by reacting an alkene with sodium nitrite, hydrochloric acid and methanol.

The nitrosochloroalkane can then be reacted with hydroxylamine, hydrochloric acid and sodium acetate to produce a hydroxylamino oxime (Formula V, below).

The hydroxylamino oxime can then be reacted with a ketone to produce a mixture of an hydroxyl and oxyl imidazoline oxide (Formulas IIa and IIe, below), which can then be oxidized by manganese dioxide (MnO$_2$) to produce oxyl imidazoline oxide (Formula IIb, below), which can be reduced by hydroxylamine to form pure hydroxylimidazoline.

Alternatively, the hydroxyl imidazoline oxide can be reacted with sodium borohydride to produce a dihydroxyl imidazolidine (Formula IIIa, below). The oxyl imidazoline oxide can be reacted with sodium borohydride to produce an oxyl hydroxyimidazolidine (Formula IIIb).

Alternatively, the hydroxylamino oxime can be reacted with concentrated hydrochloric acid and water to produce hydroxylamino ketone. The hydroxylamino ketone can then be reacted with a ketone and ammonium hydroxide to produce a mixture compounds of formulas IIc, IId and IIe, below, which can then be oxidized with MnO$_2$ to produce oxyl imidazoline (Formula IId, below).

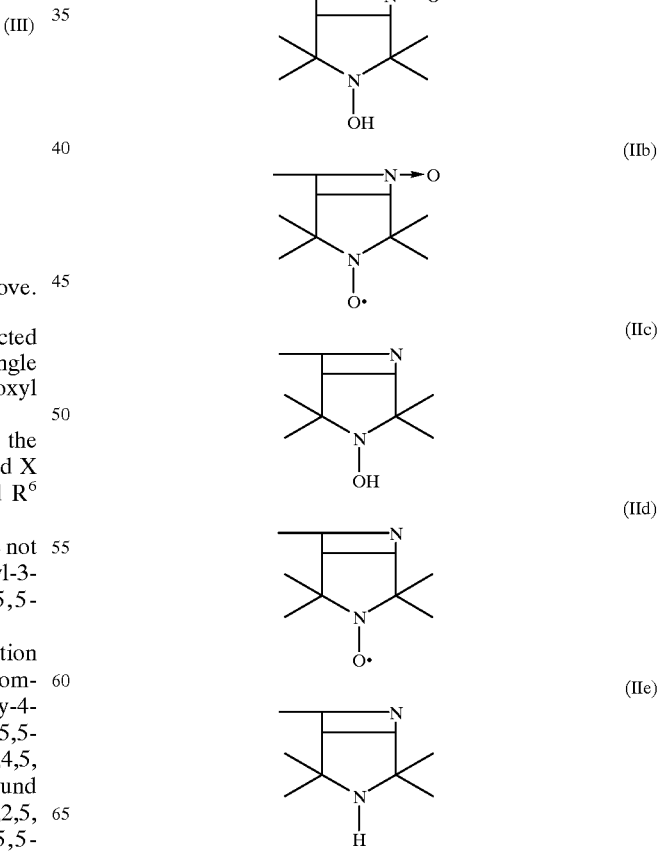

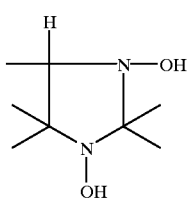

(IIIa)

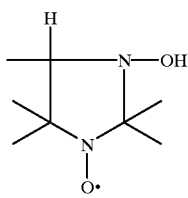

(IIIb)

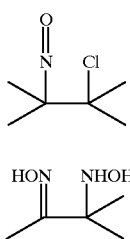

(IV)

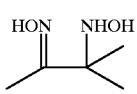

(V)

The following examples are presented for the purpose of illustration only and are not to be construed as limiting the present invention.

EXAMPLE 1

Preparation of a nitrosochloroalkane from an alkene was accomplished by charging 72.3 g sodium nitrite and 360 ml. methanol to a flask and cooling the mixture to −15.3° C. Then 41.9 g of trimethylethylene (2-methyl-2-butene) was added and the mixture was cooled to −19.8° C. 244.7 ml hydrochloric acid (36% concentration HCl) was added over a period of 2 hrs. after which the mixture was allowed to react for 4 hrs at a temperature between −15.2° C. and −19.5° C. Afterwards the mixture was poured into iced water, washed and filtered. The product was 81.3 g of 2-chloro-2-methyl-3-nitrosobutane.

EXAMPLE 2

Preparation of an hydroxylamino oxime from a nitrosochloroalkane was accomplished by preparing an aqueous first solution (0.504 g/ml) of hydroxylamine hydrochloride (NH$_2$OH.HCl/H$_2$O), mixing 112 ml isopropanol in water to achieve a 0.8025 g/ml solution which was then used to dissolve 60.5 g sodium acetate to achieve a 0. 1025 g/ml second solution of CH$_3$COONa/CH$_3$CHOHCH$_3$—H$_2$O. The first and second solutions were then combined in a flask at ambient temperature and 50 g of 2-chloro-2-methyl-3-nitrosobutane were added to flask. The contents of the flask were reacted at 67.1 ° C. for 2.5 hrs. The mixture was allowed to remain in the flask overnight. The isopropanol was then removed under vacuum and heat. The resulting filtered and washed product was 53.5 g 2-hydroxylamino-2-methyl-3-oximebutane acetate.

EXAMPLE 3

Preparation of a mixture of an oxylimidazoline oxide and hydroxyimidazoline oxide from a hydroxylamino oxime was accomplished by mixing 50.07 g 2-hydroxylamino-2-methyl-3-oximepentane acetate, 500 ml acetone, and 10 ml hydrochloric acid (5% concentration) in a flask, refluxing for 24 hrs. 25 min. at 58° C., evaporating the solvent, then refrigerating the flask adding an equal volume of ether, filtering, rinsing with ether and drying. The product was 8.5 g of a mixture containing 52.4% of 1-hydroxy-4-ethyl-2,2,5,5-tetramethyl-3-imidazoline-3-oxide and 43.2% of 1-oxyl-4-ethyl-2,2,5,5-tetramethyl-3-imidazoline-3-oxide.

EXAMPLE 4

Preparation of an oxyl imidazoline oxide from a hydroxyl imidazoline oxide was achieved by combining 50.0 g of the product mixture produced in accordance with Example 3, 20 g MnO$_2$ and 500 ml ethyl acetate in a flask at room temperature, stirring for 1 hr 15 min., filtering twice, evaporating the ethyl acetate, drying and recrystallizing with ethyl acetate. The product was 54.51 g of 1-oxyl-2,2,4,5,5-pentamethyl-3-imidazoline-3-oxide.

EXAMPLE 5

Preparation of a hydroxylamino ketone from an hydroxylamino oxime was achieved by mixing 50 g of 2-hydroxylamino-2-methyl-3-oximebutane acetate and 100 ml of hydrochloric acid (36% concentration) in a flask, allowing the mixture to react for 20–22 hrs at −5° C. The product was then filtered, rinsed with distilled water, dried by evaporation then recrystallized from an acrylonitrile solvent. A product of 35 g of 2-hydroxylamino-2-methyl-3-butanone was obtained.

EXAMPLE 6

Preparation of a mixture of an oxylimidazoline and hydroxylimidazoline from an hydroxylamino ketone was achieved by mixing 10.0 g of 2-hydroxylamino-2-methyl-3-pentanone hydrochloride and 50 ml acetone in a flask, adding 20 ml ammonium hydroxide (30% concentration), stirring at room temperature for 1 hr, then evaporating the acetone. The flask was then refrigerated overnight and the crystals of product were filtered and dried. The product was 1.3 g of a mixture containing 55.1 % of 1-hydroxy-4-ethyl-2,2,5,5-tetramethyl-3-imidazoline and 42.1 % of 1-oxyl-4-ethyl-2,2,5,5-tetramethyl-3-imidazoline.

EXAMPLE 7

Preparation of an oxyl imidazoline from an hydroxylamino ketone was achieved by mixing 16.5 g of 2-hydroxylamino-2-methyl-3-pentanone hydrochloride, 19.6 g of cyclohexanone, and 29 ml of ammonium hydroxide (30% concentration) in a flask while maintaining the flask at room temperature for 1 hr. The contents of the flask were then extracted with ether. The ether layer was separated and MgSO$_4$ was added to the ether as a drying agent. The MgSO$_4$ was then filtered out. Then, the ether solution was oxidized by 2.1 g MnO$_2$ for 1 hr., filtered, then dried by evaporation to remove ether and water. Additional ether and 8 ml deionized water were added and the layers of liquid were separated. MgSO$_4$ was added to the organic layer, which was then stirred for 1 hr. and filtered out. The ether was removed by evaporation from the liquid, which was then refrigerated at −7° C. to crystallize. A product of 9.25 g of 2-cyclohexanone-4-ethyl-5,5-dimethyl-3-imidazoline-1-oxyl was obtained.

EXAMPLE 8

2 g of the amide of 1-oxyl-2,2,5,5-tetramethyl-3-oxide-3-imidazoline-4-carbonic acid (Formula VIa, below) was dissolved in 25 ml of 10% KOH, then 1.2 g NaBrO was added and the mixture was stirred for 4 hrs. The resulting compound was 1-oxyl-3-hydroxy-4-oxo-2,2,5,5-tetramethyl-3-imidazolidine (Formula VIb), which was then extracted with ethyl acetate. The solution was dried with MgSO$_4$ and evaporated. 1 g of compound Vb was then further reduced by 0.5 g hydroxylamine in 25 ml ether to form 0.7 g of 1,3-dihydroxy-4-oxo-2,2,5,5-tetramethyl-3-imidazolidine having Formula VIc, below.

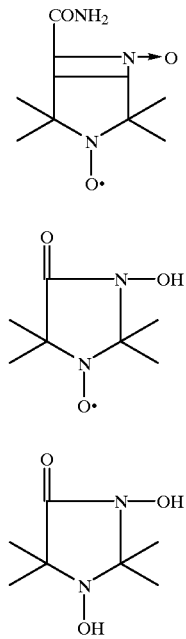

EXAMPLE 9

10 g of 1-oxyl-2,2,4,5,5-pentamethyl-3-imidazoline was dissolved in 100 ml of dried ether and 4 g of hydroxylamine were added. The mixture was stirred for 5 hrs, dried with MgSO$_4$ and the ether was then evaporated. The product 8.2 g of 1-hydroxy-2,2,4,5,5-pentamethyl-3-imidazoline was recrystallized from ethylacetate.

EXAMPLES 10–19

In these examples the effectiveness of the polymerization inhibitors of the present invention in preventing polymerization of styrene was measured. The styrene was purified to remove all traces of tert-butyl catechol (TBC). All of the samples were tested in accordance with the following procedure:

A 40 g test quantity of TBC-free styrene containing 100 ppm of inhibitor was charged to a three neck 50ml round bottom flask fitted with a thermometer and a reflux condenser whose top opening was fitted with a septum through which an 18 gauge syringe needle was inserted. The flask was also fitted with a gas inlet tube and a magnetic stirrer. A constant temperature silicone oil bath was used to control the temperature. The styrene was prepurged with nitrogen to remove dissolved oxygen prior to being heated in the oil bath.

When the styrene reached the desired temperature of 116° C. air was sparged into the flask at 5 cc/min. Samples of the test styrene were removed at regular intervals of time and the refractive index of the styrene was measured to determine the polymer content. The relative effectiveness of inhibition of the various polymerization inhibitors tested is reported in terms of an induction period, which is the length of time elapsed before the level of polymer in the styrene sample has reached 1% or higher. Thus, the longer the induction period the more effective was the polymerization inhibitor.

The results are set forth below in Table 1. Multiple sampling results are shown for some examples.

TABLE 1

| Exmpl. | Inhibitor | Induction Time (min) | % Polymer |
|---|---|---|---|
| 10 | 1-oxyl-2,2,4,5,5-pentamethyl-3-imidazoline | 81 | 1.5 |
| 11 | 1-oxyl-2,2,4,5,5-pentamethyl-3-imidazoline-3-oxide | 71 | 1.33 |
| 12 | 1-oxyl-4-ethyl-2,2,5,5-tetramethyl-3-imidazoline | 61 | 1.5 |
|  |  | 65 | 2.49 |
| 13 | mixture of 1-hydroxy-4-ethyl-2,2,5,5-tetramethyl-3-imidazoline (40–45%) and 1-oxyl-4-ethyl-2,2,5,5-tetramethyl-3-imidazoline (40–45%) | 73 | 1.0 |
|  |  | 78 | 1.0 |
|  |  | 75 | 1.33 |
| 14 | 1,2,2,5,5-pentamethyl-3-imidazoline-3-oxide | 20 | 2.66 |
| 15 | 1-nitro-2,2,5,5-tetramethyl-3-imidazoline-3-oxide | 18 | 1.99 |
| 16 | 1-hydroxy-2-(2,2,6,6-tetramethyl-piperidino-1-oxyl)-4,5,5-trimethyl-3-imidazoline | 88 | 1.33 |
| 17 | 1-oxyl-2-cyclohexane-4-ethyl-5,5-dimethyl-3-imidazoline | 58 | 1.83 |
| 18 | mixture of 1-hydroxy-2,2,4,5,5-pentamethyl-3-imidazoline (51.9–55.1%) and 1-oxyl-2,2,4,5,5-pentamethyl-3-imidazoline (31.2%–34.2%) | 62 | 1.83 |
|  |  | 96 | 1.99 |
|  |  | 99 | 1.83 |
| 19 | 1,3-dihydroxy-2,2,4,5,5-pentamethyl-3-imidazolidine | 58 | 4.82 |

EXAMPLE 20

A first blend was made by premixing 1 part 1-hydroxy-2,2,4,5,5-pentamethyl-3-imidazoline and 1 part 1-oxyl-2,2,4,5,5-pentamethyl-3-imidazoline with heating to a temperature of 50° C. This blend was then tested for polymerization inhibition of styrene in accordance with the method of Examples 10–19. The blend exhibited an induction time of 97 minutes with a corresponding polymer level of 1.33%.

A second blend of the same composition percentages as the first blend and made in the same manner exhibited an induction time of 95 minutes with a corresponding polymer level of 1.66%.

A third blend of the same composition percentages as the first blend and made in the same manner exhibited an induction time of 76 minutes and a corresponding polymer level of 1.66%.

EXAMPLE 21

1 part 1-hydroxy-2,2,4,5,5-pentamethyl-3-imidazoline and 1 part 1-oxyl-2,2,4,5,5-pentamethyl-3-imidazoline were mixed in situ in a test sample of styrene to a concentration of 100 ppm of blended inhibitor, which was then tested for polymerization inhibition in accordance with the method of Examples 10–19. The blend exhibited an induction time of 81 minutes with a corresponding polymer level of 1.66%.

EXAMPLE 22

1 part 1-hydroxy-2,2,4,5,5-pentamethyl-3-imidazoline and 2 parts 1-oxyl-2,2,4,5,5-pentamethyl-3-imidazoline were mixed in situ in a test sample of styrene to a concentration of 100 ppm of blended inhibitor, which was then tested for polymerization inhibition in accordance with the method of Examples 10–19. The blend exhibited an induction time of 82 minutes with a corresponding polymer level of 1.66%.

EXAMPLE 23

A blend was made by premixing 1 part 1-hydroxy-2,2,4,5,5-pentamethyl-3-imidazoline and 2 parts 1-oxyl-2,2,4,5,5-pentamethyl-3-imidazoline with heating at a temperature of 50° C. This blend was then tested for polymerization inhibition of styrene in accordance with the method of Examples 10–19. The blend exhibited an induction time of 78 minutes with a corresponding polymer level of 1.00%.

EXAMPLE 24

2 parts 1-hydroxy-2,2,4,5,5-pentamethyl-3-imidazoline and 1 part 1-oxyl-2,2,4,5,5-pentamethyl-3-imidazoline were mixed in situ in a test sample of styrene to a concentration of 100 ppm of blended inhibitor, which was then tested for polymerization inhibition in accordance with the method of Examples 10–19. The blend exhibited an induction time of 87 minutes with a corresponding polymer level of 1.50%.

EXAMPLE 25

3 parts 1-hydroxy-2,2,4,5,5-pentamethyl-3-imidazoline and 1 part 1-oxyl-2,2,4,5,5-pentamethyl-3-imidazoline were mixed in situ in a test sample of styrene to a concentration of 100 ppm of blended inhibitor, which was then tested for polymerization inhibition in accordance with the method of Examples 10–19. The blend exhibited an induction time of 78 minutes with a corresponding polymer level of 1.83%.

EXAMPLE 26

A blend was made by premixing 1 part 1-oxyl-2,2,4,5,5-pentamethyl-3-imidazoline and 1 part 1-oxyl-2,2,4,5,5-pentamethyl-3-imidazoline-3-oxide with heating at a temperature of 50° C. This blend was then tested for polymerization inhibition of styrene in accordance with the method of Examples 10–19. The blend exhibited an induction time of 69 minutes with a corresponding polymer level of 1.50%.

EXAMPLE 27

A first blend was made by premixing 1 part 1-hydroxy-4-ethyl-2,2,5,5-tetramethyl-3-imidazoline and 1 part 1-oxyl-4-ethyl-2,2,5,5-tetramethyl-3-imidazoline. This blend was then tested for polymerization inhibition of styrene in accordance with the method of Examples 10–19. The blend exhibited an induction time of 60 minutes with a corresponding polymer level of 1.00%.

A second blend of the same composition percentages as the first blend and made in the same manner exhibited an induction time of 71 minutes with a corresponding polymer level of 1.00%.

COMPARATIVE EXAMPLE

For purposes of comparison the effectiveness of 2,6-dinitro-p-cresol (DNPC), a known polymerization inhibitor, was tested for polymerization inhibition of styrene in accordance with the method of Examples 10–19 described above. The DNPC exhibited an induction time of 60 minutes for a corresponding polymerization level of 1.00 %.

While the above description contains many specifics, these specifics should not be construed as limitations on the scope of the invention, but merely as exemplifications of preferred embodiments thereof. Those skilled in the art will envision many other possible variations within the scope and spirit of the claims appended hereto.

What is claimed is:

1. A method for stabilizing a polymerizable ethylenically unsaturated organic compound from premature polymerization, comprising:

adding to the unsaturated organic compound an effective amount for premature polymerization inhibition, of a polymerization inhibitor including at least one compound having the formula:

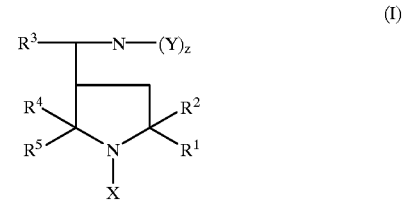

(I)

wherein X is —H, —OH, —O•, —NO₂, or —CH₃, $R^1$, $R^2$, $R^4$ and $R^5$ are the same or different and each is selected from the group consisting of hydrogen, an aliphatic moiety having from 1 to about 20 carbon atoms, aryl, alkaryl or aralkyl having from 6 to about 12 carbon atoms, alicyclic and heterocyclic, or $R^1$ and $R^2$ together or R4 and $R^5$ together form part of an alicyclic or heterocyclic moiety having from about 4 to about 10 ring members, $R^3$ is hydrogen or an aliphatic moiety having from 1 to about 20 carbon atoms, and z is 0 or 1 and where z is 1, Y is O bonded to N in the form of an N→O moiety, wherein the unsaturated organic compound is selected from the group consisting of styrene, methylstyrene, divinylbenzene, butadiene, isoprene, vinyl chloride, chloroprene, vinylidene chloride, vinylidene fluoride, vinyl fluoride, acrylic acid, methacrylic acid, crotonic acid, vinyl acetate, methyl methacrylate, ethyl acrylate, methyl acrylate, 2-hydroxyethyl acrylate, 2-hydroxyethyl methacrylate, ethylene bismethacrylate, trimethylolpropane triacrylate, acrylated epoxy resin, polyethylene glycol diacrylate, acrylamide, N,N-dimethylacrylamide, methylenebisacrylamide, N-vinylpyrrolidone, acrylonitrile, methyl vinyl ether, vinyl pyridine, diethyl vinylphosphonate and sodium styrenesulfonate.

2. The method of claim 1 wherein the polymerization inhibitor includes a compound selected from the group consisting of 1-oxyl-2,2,4,5,5-pentamethyl-3-imidazoline, 1-hydroxy-2,2,4,5,5-pentamethyl-3-imidazoline, 1-oxyl-4-ethyl-2,2,5,5-tetramethyl-3-imidazoline, 1-hydroxy-4-ethyl-2,2,5,5-tetramethyl-3-imidazoline, 1-oxyl-2,2,4,5,5-pentamethyl-3-imidazoline-3-oxide, 1,2,2,5,5-pentamethyl-3-imidazoline-3-oxide, 1-nitro-2,2,5,5-tetramethyl-3-imidazoline-3-oxide, 1-hydroxy-2-(2,2,6,6-tetramethyl-piperidino-1-oxyl)-4,5,5-trimethyl-3-imidazoline, 1-oxyl-2-cyclohexane-4-ethyl-5,5-dimethyl-3-imidazoline, and mixtures thereof.

3. The method of claim 1 wherein the unsaturated organic compound is styrene.

4. The method of claim 1 wherein unsaturated organic compound is neat.

5. The method of claim 1 wherein the unsaturated organic compound is mixed with a solvent.

6. The method of claim 5 wherein the solvent is selected from the group consisting of toluene, benzene, ethylbenzene, styrene and water.

7. The method of claim 1 wherein the effective amount of the polymerization inhibitor compound having formula (I) ranges from a concentration of about 1 ppm to 10,000 ppm by weight.

8. The method of claim 1 wherein $R^1$, $R^2$, $R^3$, $R^4$, and $R^5$, are each a moiety selected from the group consisting of methyl, ethyl, propyl and butyl, and X is —OH or —O•.

9. The method of claim 8 wherein the polymerization inhibitor includes a mixture of at least first and second compounds having formula (I) wherein in said first compound X is —OH, and z is 0, and in said second compound X is —O• and z is 0.

10. The method of claim 9 wherein said first compound is selected from the group consisting of 1-hydroxy-4-ethyl-2,2,5,5-tetramethyl-3-imidazoline and 1-hydroxy-2,2,4,5,5-pentamethyl-3-imidazoline, and the second compound is selected from the group consisting of 1-oxyl-4-ethyl-2,2,5,5-tetramethyl-3-imidazoline and 1-oxyl-2,2,4,5,5-pentamethyl-3-imidazoline.

11. The method of claim 8 further including the step of mixing a first compound selected from the group consisting of 1-hydroxy-2,2,4,5,5-pentamethyl-3-imidazoline, 1-hydroxy-4-ethyl-2,2,5,5-tetramethyl-3-imidazoline and 1-oxyl-2,2,4,5,5-pentamethyl-3-imidazoline-3-oxide, with a second compound selected from the group consisting of 1-oxyl-2,2,4,5,5-pentamethyl-3-imidazoline and 1-oxyl-4-ethyl-2,2,5,5-tetramethyl-3-imidazoline, to produce the polymerization inhibitor.

12. The method of claim 11 wherein the step of mixing the first compound with the second compound is performed prior to adding the polymerization inhibitor to the unsaturated organic compound.

13. The method of claim 12 wherein the step of mixing the first compound with the second compound is performed while heating the mixture.

14. A monomer composition stabilized against premature polymerization which includes:
a) an ethylenically unsaturated organic monomer; and
b) an effective amount for premature polymerization inhibition of component (a), of a polymerization inhibitor including at least one compound having the formula:

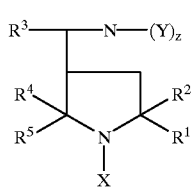

(I)

wherein X is —H, —OH, —O•, —$NO_2$, or —$CH_3$, $R^1$, $R^2$, $R^4$ and $R^5$ are the same or different and each is selected from the group consisting of hydrogen, an aliphatic moiety having from 1 to about 20 carbon atoms, aryl, alkaryl or aralkyl having from 6 to about 12 carbon atoms, alicyclic and heterocyclic, or wherein $R^1$ and $R^2$ together form part of an alicyclic or heterocyclic moiety having from about 4 to about 10 ring members,
$R^3$ is hydrogen or an aliphatic moiety having from 1 to about 20 carbon atoms, and z is 0 or 1 and where z is 1, Y is O bonded to N in the form of an N→O moiety, wherein the unsaturated organic monomer is a compound selected from the group consisting of styrene, methylstyrene, divinylbenzene, butadiene, isoprene, vinyl chloride, chloroprene, vinylidene chloride, vinylidene fluoride, vinyl fluoride, acrylic acid, methacrylic acid, crotonic acid, vinyl acetate, methyl methacrylate, ethyl acrylate, methyl acrylate, 2-hydroxyethyl acrylate, 2-hydroxyethyl methacrylate, ethylene bismethacrylate, trimethylolpropane triacrylate, acrylated epoxy resin, polyethylene glycol diacrylate, acrylamide, N,N-dimethylacrylamide, methylene-bisacrylamide, N-vinylpyrrolidone, acrylonitrile, methyl vinyl ether, vinyl pyridine, diethyl vinylphosphonate and sodium styrenesulfonate.

15. The method of claim 13 wherein the mixture is heated to 50° C.

16. The composition of claim 14 wherein the unsaturated organic monomer is styrene.

17. The composition of claim 14 wherein the effective amount of the polymerization inhibitor compound having formula (I) ranges from a concentration of about 1 ppm to 10,000 ppm by weight.

18. The method of claim 16 wherein the first compound and second compound are mixed in situ in the unsaturated organic compound.

19. The composition of claim 18 wherein $R^1$, $R^2$, $R^3$, $R^4$, and $R^5$, are each a moiety selected from the group consisting of methyl, ethyl, propyl and butyl groups, and X is —OH or —O•.

20. The method of claim 19 wherein the polymerization inhibitor includes a mixture of at least first and second compounds having formula (I) wherein in said first compound X is —OH, and z is 0, and in said second compound X is —O• and z is 0.

21. The method of claim 20 wherein said first compound is selected from the group consisting of 1-hydroxy-4-ethyl-2,2,5,5-tetramethyl-3-imidazoline and 1-hydroxy-2,2,4,5,5-pentamethyl-3-imidazoline, and the second compound is selected from the group consisting of 1-oxyl-4-ethyl-2,2,5,5-tetramethyl-3-imidazoline and 1-oxyl-2,2,4,5,5-pentamethyl-3-imidazoline.

22. The method of claim 11 wherein from 1 to 3 parts of the first compound are mixed with from 1 to 2 parts of the second compound.

23. The composition of claim 14 wherein the polymerization inhibitor includes a compound selected from the group consisting of 1-oxyl-2,2,4,5,5-pentamethyl-3-imidazoline, 1-hydroxy-2,2,4,5,5-pentamethyl-3-imidazoline, 1-oxyl-4-ethyl-2,2,5,5-tetramethyl-3-imidazoline, 1-hydroxy-4-ethyl-2,2,5,5-tetramethyl-3-imidazoline, 1-oxyl-2,2,4,5,5-pentamethyl-3-imidazoline-3-oxide, 1,2,2,5,5-pentamethyl-3-imidazoline-3-oxide, 1-nitro-2,2,5,5-tetramethyl-3-imidazoline-3-oxide, 1-hydroxy-2-(2,2,6,6-tetramethyl-piperidino-1-oxyl)-4,5,5-trimethyl-3-imidazoline, 1-oxyl-2-cyclohexane-4-ethyl-5,5-dimethyl-3-imidazoline, and blends thereof.

24. The composition of claim 14 further including one or more additives selected from the group consisting of metal deactivators, UV absorbers, stabilizers to retard acid-catalyzed degradation, thermal initiators and photoinitiators.

* * * * *

UNITED STATES PATENT AND TRADEMARK OFFICE
CERTIFICATE OF CORRECTION

PATENT NO. : 6,287,483 B1  
APPLICATION NO. : 09/084619  
DATED : September 11, 2001  
INVENTOR(S) : John M. DeMassa and Stephen M. Fagan It is certified that error appears in the above-identified patent and that said Letters Patent is hereby corrected as shown below:

Claim 1, column 12, lines 15-21, the chemical formula should appear as follows:

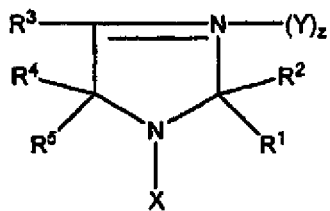

Claim 14, column 13, lines 46-52, the chemical formula should appear as follows:

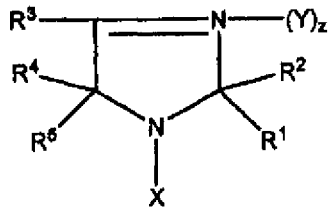

Signed and Sealed this

Seventeenth Day of November, 2009

David J. Kappos  
*Director of the United States Patent and Trademark Office*